United States Patent [19]

Gottwald et al.

[11] Patent Number: 5,057,319

[45] Date of Patent: Oct. 15, 1991

[54] PHARMACEUTICAL COMPOSITIONS OF CIMETIDINE

[75] Inventors: Eberhard F. Gottwald; Hermann P. Osterwald, both of Bovenden; Horst M. Machoczek, Gleichen, all of Fed. Rep. of Germany; David Mayron, Blue Bell, Pa.

[73] Assignee: Smith Kline Dauelsberg GmbH, Gottingen, Fed. Rep. of Germany

[21] Appl. No.: 287,194

[22] Filed: Dec. 20, 1988

[30] Foreign Application Priority Data

Dec. 23, 1987 [GB] United Kingdom ............ 8730011

[51] Int. Cl.$^5$ .................................. A61K 9/28
[52] U.S. Cl. .................... 424/441; 424/438; 424/437
[58] Field of Search ................. 424/441, 438, 437

[56] References Cited

U.S. PATENT DOCUMENTS

| 3,308,217 | 3/1967 | Lowey et al. | 264/117 |
| 4,256,108 | 3/1981 | Theeuves | 424/437 |
| 4,814,183 | 3/1989 | Zantner | 424/444 |
| 4,824,675 | 4/1989 | Wong et al. | 424/438 |
| 4,851,228 | 7/1989 | Zentner et al. | 424/438 |
| 4,892,778 | 1/1990 | Theeuves et al. | 424/457 |

FOREIGN PATENT DOCUMENTS

| 0195476A | 10/1986 | European Pat. Off. |
| 0208144 | 1/1987 | European Pat. Off. |
| 2253507 | 12/1973 | France . |
| 2593065 | 7/1987 | France . |
| 2081092A | 7/1981 | United Kingdom . |
| 2119247A | 4/1983 | United Kingdom . |
| 2195892A | 10/1987 | United Kingdom . |
| 2195890A | 4/1988 | United Kingdom . |
| 2195891A | 4/1988 | United Kingdom . |

OTHER PUBLICATIONS

Chemical Abstracts, vol. 85, 1976, p. 339, abstract 51748n.
Chemical Abstracts, vol. 96, 1982, p. 423. abstract 149173y.
Chemical Abstracts, vol. 97, 1982, pp. 370-371, abstract 11885g.
Derwent Abs. 42988 K/18.
Derwent Abs. 37914 E/19.
Derwent Abs. 80-17687C/10 (Eng. Trans. of Jap. 86228/78).

Primary Examiner—Thurman K. Page
Assistant Examiner—William Benston
Attorney, Agent, or Firm—Stuart R. Suter; Edward T. Lentz

[57] ABSTRACT

The present invention provides a pharmaceutical granule composition comprising cimetidine and, as a granulating agent and taste-masking agent, an ester of a polyhydroxy compound, and where desired a palatable pharmaceutically acceptable emulsifier. Particular esters are glycerol esters. The granules of the present invention can be used in the preparation of chewable tablets which have good palatability and bioavailability.

20 Claims, No Drawings

PHARMACEUTICAL COMPOSITIONS OF CIMETIDINE

This invention relates to granules of cimetidine which are useful in the preparation of tablets and which have an improved flavour.

Cimetidine is a histamine $H_2$-antagonist which has been described in U.K. Patent Specification 1.397.436. Cimetidine has been shown to be useful in the treatment of duodenal, gastric, recurrent and stomal ulceration, and reflux oesophagitis and in the management of patients who are at high risk from haemorrhage of the upper gastrointestinal tract.

Cimetidine is known to have a pronounced bitter taste. This is not usually a problem when the dosage form employed is a capsule or a tablet designed to be swallowed, thereafter to disintegrate upon reaching the stomach. However, such dosage forms can be impractical when it is desired to administer a large amount of active ingredient, or to co-administer a relatively bulky second active ingredient such as an antacid or alginate. Moreover many individuals have difficulty in swallowing a solid dosage form.

A conventional approach to administering relatively large amounts of active ingredient in a solid dosage form is by means of a chewable tablet, i.e. a tablet which disintegrates in the mouth upon being chewed. Such a tablet also circumvents the problem of a solid dosage being difficult to swallow.

It will be appreciated that a major requirement of such a dosage form is that it must be palatable, since an unpalatable formulation increases the risk of a patient neglecting to rake the tablet. Such non-compliance with the dosing regimen will in turn delay or prevent the patient's recovery from the condition under treatment.

A further requirement of such a composition is that once the disintegrated tablet reaches the stomach, the individual particles should release the active ingredient rapidly and completely in order to ensure that substantially all of the active ingredient is absorbed; that is to say the formulation should be bioavailable.

In the case of cimetidine, because of its bitterness, the provision of such a dosage form represents a considerable problem.

Several solutions to this problem have been proposed. One proposal is disclosed in Japanese Patent Application No. 67375/80 wherein there are described granules of cimetidine containing ethylcellulose preferably in the range of 15 to 85% (w/w) and particularly preferably 50% (w/w) relative to the cimetidine. Such granules are described as having good stability to light, good dissolution characteristics and are stated not to have a bitter taste. These properties are stated to be specific to granules containing ethylcellulose; it is disclosed that methylcellulose does not impart such properties.

Another proposed solution is disclosed in Japanese Patent Application No. 86228/78 which similarly describes cimetidine granules containing a polymeric substance; in this case specifically polyvinylacetal diethylaminoacetate.

One general approach to the masking of the taste of bitter medicaments has been to coat the medicament with a waxy, fatty or oily substance.

Thus, for example, British Patent No. 2,081,092 discloses the use of waxy substances to mask the bitter taste of certain medicaments. Particular waxy substances mentioned are carnauba wax, beeswax, solid fats and oils such as castor wax, acetoglyceride, higher fatty acids such as stearic acid, palmitic acid and higher alcohols such as cetyl alcohol and stearyl alcohol. However, GB 2,081,092 also discloses that, in order to avoid the known problem of the waxy substance retarding the dissolution and absorption of the active ingredient, it is necessary also to include in the formulation a water-swellable high molecular weight material such as cross-linked polyvinylpyrrolidone.

Fats and oils are composed mainly of triglycerides, i.e. glycerol in which all three hydroxyl groups have been esterified with fatty acids. In the pharmaceutical field, such triglycerides are used mainly as suppository bases or as constituents of ointments and creams.

Partially hydrolysed glycerides such as mono- and di-glycerides are also known to be used in the preparation of pharmaceutical compositions but these are in general employed as emulsifiers and emulsion stabilisers, for example in oil-in-water and water-in-oil emulsions.

A further known use of glycerol esters is as release-retarding coatings in sustained release formulations. For example, British Patent Application GB 2,119,247A discloses a sustained release tablet of lithium carbonate in which the release-retarding agent is a mixture of glyceryl mono-, di- and tri-esters of one or more straight chain fatty acids. The sustained release formulations disclosed in GB 2,119,247A optionally contain a surfactant such as sodium lauryl sulphate.

Surprisingly, we have now found that a cimetidine granule which has good palatability but also has good dissolution characteristics can be prepared by granulating the cimetidine with an ester of a polyhydroxy compound. Such granules need not contain a water-swellable high molecular weight substance of the type disclosed in GB 2,081,092.

By polyhydroxy compound is meant a non-polymeric non-aromatic hydrocarbon or carbohydrate compound having at least two and preferably no more than ten hydroxyl groups per molecule. Examples of polyhydroxy compounds include the alkane polyols such as glycerol, the sugar alcohols, e.g. mannitol, and mono- and di-saccharides such as glucose and sucrose.

By ester is meant a polyhydroxy compound in which at least one of the hydroxyl groups has been esterified with a $C_{6-24}$ fatty acid. Particularly a $C_{12-24}$ fatty acid such as stearic acid or palmitic acid. Particular esters are mixtures of monoesters and/or diesters and/or tri-esters or substantially pure monoesters and diesters.

Preferred esters are glycerol esters and sucrose esters.

The type and quantity of the esters employed in the granules of the present invention is selected such that the bitter taste of the cimetidine is masked and preferably such that the granules have dissolution characteristics whereby 90% by weight of the cimetidine in a granule dissolves within about 50 minutes as measured using the US Pharmacopoeia Paddle test (paddle speed 100 r.p.m.)(USP XXI, pp.1243–1244).

The ester, for example a glycerol ester or sucrose ester, is usually present in an amount corresponding to at least 15% and suitably from 15% to 100% by weight relative to the cimetidine; particularly approximately 20% when the ester is a glycerol ester.

The glycerol esters available commercially frequently are provided as a mixture of mono-, di- and tri-glycerides of various fatty acids. For example, commercially available glyceryl monostearate is often provided as a mixture comprising mainly glyceryl monostearate and glyceryl monopalmitate, as well as variable quantities of di- and tri-glycerides. The US Pharmacopoeia (USP XXI/NF XVI, p.1565) definition of glyceryl monostearate refers to a mixture containing not less than 90% of monoglycerides of saturated fatty acids whereas the British Pharmacopoeia (BP 1980, pp.212-213) defines glyceryl monostearate as a mixture containing not less than 35% of monoglycerides. Because glycerol esters are usually provided as mixtures, it is most convenient to define them in terms of their bulk properties and in particular their chemical reactivities towards certain standard reagents. One such property which will be used herein to define the glycerol esters of the present invention is the hydroxyl value.

The hydroxyl value of a glycerol ester is a measure of the number of free hydroxyl groups and is defined in the US Pharmacopoeia (USP XXI, p.1200) as the number of mg. of potassium hydroxide equivalent to the hydroxyl content of 1.0 g of the substance.

Particular glycerol esters are those selected from:
a) glycerol esters having a hydroxyl value of greater than 120:
b) glycerol esters having a hydroxyl value of greater than 60 and having a triglyceride content of less than 30% by weight; and
c) glycerol esters having a hydroxyl value of greater than b and a melting point of less than 40° C.

Examples of glycerol esters in category a) are those which are composed mainly of monoglycerides, such as glyceryl monostearate, and which have a hydroxyl value of at least 195. Preferably the monoglyceride content is at least 50% by weight of the total weight of the ester. Particular examples of such esters are those marketed under the trade names Dur EM and Monomuls.

Dur EM is a mixture of α- and β-monostearates and diglycerides; the α-monostearate being present as approximately 52% by weight of the ester.

Monomuls is a mixture containing approximately 57-62% glyceryl monostearate.

Examples of glycerol esters in category b) include substantially pure glyceryl distearate and examples of glycerol esters in category c) are those sold under the trademark Witepsol as Witepsol H 15, Witepsol H 19 and Witepsol W 45. The aforementioned Witepsols have an ascending melting point in the range 33.5-35.5 and hydroxyl values of 15 (maximum). 20-30 and 40-50 respectively.

Witepsol W 45 is composed of approximately 8% (w/w) monoglyceride, 10-12% (w/w) diglyceride, approximately 80% (w/w) triglyceride and less than 0.2% (w.w) glycerol.

Preferred glycerol esters are those selected from category a).

Examples of sucrose esters are mixtures of mono-, di- and tri-esters. Particularly those formed from palmitic and stearic acids, for example esters formed from a 30:70 mixture of palmitic:stearic acids. Particular esters are those having a hydroxyl value of greater than 130, and melting points in the range 70°-80° C., for example those sold under the trade names Crodesta F50 and Crodesta F160 by Croda Chemicals Ltd., Goole, North Mumberside, U.K. Crodesta F50 and F160 have melting points of 74°-78° C. and 70°-74° C. respectively and have a monoester content of 29% and 75% respectively.

It has also been found that by including a palatable pharmaceutically acceptable emulsifier in the granules, their dissolution rate can be increased still further without reducing palatability. Typically, the emulsifier can be present in an amount up to approximately 200% by weight, for example approximately 100% by weight, relative to the glycerol ester. One class of pharmaceutically acceptable emulsifiers is the lecithins.

Preferably the lecithin contains no unsaturated fatty acids. One such lecithin is soya lecithin, particularly soya lecithin NC 95 H which contains more than 87% phosphatidyl choline, not more than 5% lysolecithin and a fatty acid component consisting of 8-12% palmitic acid and 84-88% stearic acid.

In one preferred aspect of the invention, the granulating agent is a mixture of a glycerol ester containing at least 50% by weight of a monoglyceride and having a hydroxyl value of at least 195, and soya phosphatide each of which is present in an amount approximating to 20% by weight relative to the cimetidine.

Granules comprising cimetidine, an ester such as a sucrose or glycerol ester and optionally an emulsifier such as a lecithin as described hereinbefore are particularly useful in the preparation of chewable tablets, and hence chewable tablets containing such granules represent a further embodiment of this invention.

The chewable tablets of this invention contain normally at least 75 mg of cimetidine. As a maximum the tablet will not normally contain more than 800 mg of cimetidine, preferably it contains 100 or 200 mg of cimetidine.

The tablets of the invention can also contain a hydroxide or carbonate antacid. Examples of suitable antacids include aluminium hydroxide, magnesium hydroxide, magnesium carbonate, calcium carbonate and co-dried gels for example aluminium hydroxide-magnesium carbonate co-dried gel. In practice the quantity of antacid is usually between 5 milliequivalents per tablet and 40 milliequivalents, typically approximately 15 milliequivalents.

The tablets can also contain solid diluents, for example sugars such as sucrose and lactose, and sugar alcohols such as xylitol, sorbitol and mannitol. When the solid diluent is a sugar alcohol, particularly sorbitol or mannitol, it is preferred that the cimetidine granules also contain an emulsifier such as a lecithin.

The tablets can also contain sweeteners, flavours and enhancers such as ammonium glycyrrhizinate, aspartame, sodium cyclamate and sodium saccharinate, sodium chloride, sodium glutamate and Contramarum; and tableting starch to enhance palatability and mouth feeling.

The tablets can also contain other standard tableting excipients for example a binder and a disintegrant.

Where the tablet contains an antacid, preferably the antacid is pre-compressed or granulated before it is mixed with the cimetidine granules.

The cimetidine granules can be prepared by adding the ester or an ester/lecithin mixture to cimetidine (which optionally has been pre-heated to a temperature slightly below the melting point of the ester) and warming the mixture, by external heating or by high speed agitation, until the ester just melts. Mixing is continued for a short period of time until the mixture just granulates. In this way, within a few minutes, coated granules substantially free of agglomerates are obtained.

The granules can also be prepared by granulation in a spray-dryer according to conventional techniques.

It is preferred that prior to granulating, 90% of the cimetidine particles have an apparent diameter of less than 70 microns.

The granules can be sieved to remove fine particles and larger particles. Preferably the granules pass through a 1 mm sieve but are retained by a 0.2 mm sieve.

The cimetidine granules and the antacid (preferably granulated) are then mixed with conventional tablet excipients as described hereinbefore and compressed into tablets using the appropriate punches and dies.

The following Examples illustrate the invention.

EXAMPLES 1-7

| Chewable Tablet Containing Cimetidine/Glycerol Ester Granules and Antacid | | | | | | | |
|---|---|---|---|---|---|---|---|
| | 1 | 2 | 3 | 4 | 5 | 6 | 7 |
| Cimetidine | 100.0 | 100.0 | 200.0 | 100.0 | 100.0 | 200.0 | 200.0 |
| Dur EM | 20.0 | — | 40.0 | 20.0 | 20.0 | 40.0 | 40.0 |
| Glycerol distearate (90%) | — | 20.0 | — | — | — | — | — |
| Soyaphosphatide | — | — | — | — | 20.0 | — | 40.0 |
| F-MA 11* | 300.0 | 300.0 | 300.0 | 300.0 | 300.0 | 300.0 | 300.0 |
| Mg(OH)$_2$ | 200.0 | 200.0 | 200.0 | 200.0 | 200.0 | 200.0 | 200.0 |
| Mannitol | 676.5 | 676.5 | 556.5 | — | 656.5 | — | — |
| Xylitol | — | — | — | 676.5 | — | — | — |
| Sucrose | — | — | — | — | — | 556.5 | 516.5 |
| Microcrystalline Cellulose/ Sodium Carboxymethyl cellulose (Avicel RC 581) | 50.0 | 50.0 | 50.0 | 50.0 | 50.0 | 50.0 | 50.0 |
| Glycine | 25.0 | 25.0 | 25.0 | 25.0 | 25.0 | 25.0 | 25.0 |
| Sodium cyclamate | 50.0 | 50.0 | 50.0 | 50.0 | 50.0 | 50.0 | 50.0 |
| Sodium carboxymethyl cellulose | 5.0 | 5.0 | 5.0 | 5.0 | 5.0 | 5.0 | 5.0 |
| Sodium chloride | 12.5 | 12.5 | 12.5 | 12.5 | 12.5 | 12.5 | 12.5 |
| Sodium glutamate | 5.0 | 5.0 | 5.0 | 5.0 | 5.0 | 5.0 | 5.0 |
| Hydroxypropylmethyl cellulose (Methocel E 5) | 25.0 | 25.0 | 25.0 | 25.0 | 25.0 | 25.0 | 25.0 |
| Calcium arachinate | 20.0 | 20.0 | 20.0 | 20.0 | 20.0 | 20.0 | 20.0 |
| Aerosil 200 | 3.0 | 3.0 | 3.0 | 2.0 | 3.0 | 3.0 | 3.0 |
| Flavours | 8.0 | 8.0 | 8.0 | 8.0 | 8.0 | 8.0 | 8.0 |

*F-MA 11 is an aluminium hydroxide-magnesium carbonate co-dried gel.

For each of the formulations, the manufacturing process is as follows:

The cimetidine, glycerol ester (or sucrose ester see Examples 8-9) and, where appropriate, soya lecithin (soya phosphatide) are mixed in a vacuum mixer with heating in order to melt the glycerol ester. The resulting granules are sieved through a 1 mm mesh sieve.

Antacid granules are prepared by pre-mixing the FMA-11, Mg(OH)$_2$, Avicel, Glycine and sodium cyclamate and then adding the Blanose, sodium chloride, aspartame, sodium glutamate and Methocel, and water as required. The resulting granules are dried in a fluid bed drier.

The cimetidine granules are mixed with the antacid granules, the mannitol, xylitol, calcium arachinate, Aerosil and the flavouring agent to give a mixture which is compressed into tablets in a conventional manner.

EXAMPLES 8-9

Chewable Tablet Containing Cimetidine/Sucrose Ester Granules and an Antacid

The following tablets were prepared according to the method described in Examples 1-7.

| | 8 | 9 |
|---|---|---|
| Cimetidine | 100 | 200 |
| *Crodesta F50 | 25 | — |
| *Crodesta F160 | — | 50 |
| F-MA 11 | 300 | 300 |
| Mg(OH)$_2$ | 200 | 200 |
| Sucrose | 671.5 | 546.5 |
| Microcrystalline cellulose/Sodium Carboxymethyl cellulose (Avicel RC 581) | 50 | 50 |
| Glycine | 25 | 25 |
| Sodium Cyclamate | 50 | 50 |
| Sodium Carboxymethyl cellulose | 5 | 5 |
| Sodium chloride | 12.5 | 12.5 |
| Sodium glutamate | 5 | 5 |
| Hydroxypropylmethyl cellulose (Methocel E5) | 25 | 25 |
| Calcium arachinate | 20 | 20 |
| Aerosil 200 | 3 | 3 |
| Flavours | 8 | 8 |

*Crodesta F50 and F160 are mixtures of mono-, di- and tri-esters of 30:70 palmitic:-stearic acid.

| Dissolution of Compositions of the invention | | | | | | | | | | |
|---|---|---|---|---|---|---|---|---|---|---|
| Example No. | Cimetidine (mg) | Glycerol Ester (Quantity-mg) | Lecithin | Sweetener | Dissolution (%)* | | | | Hardness (Newtons) | Weight (g) |
| | | | | | 15' | 30' | 45' | 60' | | |
| 1 | 100 | Dur EM (20) | — | Mannitol | 68 | 88 | 91 | 97 | 49.0 | 1.498 |
| 4 | 100 | Dur EM (20) | — | Xylitol | 48 | 85 | 90 | 95 | 55.0 | 1.497 |
| 5 | 100 | Dur EM (20) | 20 | Mannitol | 74 | 95 | 96 | 98 | 52.0 | 1.514 |
| 6 | 200 | Dur EM (40) | — | Sucrose | 17 | 39 | 50 | 61 | 56.0 | 1.503 |
| 7 | 200 | Dur EM (40) | 40 | Sucrose | 16 | 28 | 50 | 50 | 57.7 | 1.499 |
| 8 | 100 | Crodesta F50 (25) | — | Sucrose | 26 | 55 | 80 | 95 | 77.6 | 1.498 |
| 9 | 200 | Crodesta F160 (50) | — | Sucrose | 25 | 50 | 65 | 84 | 72.0 | 1.502 |
| 10+ | 200 | Dur EM (40) | — | Mannitol | 44 | 77 | 93 | 96 | 68.0 | 1.491 |
| 11** | 200 | Dur EM (40) | — | Xylitol | 31 | 45 | 62 | 93 | 67.0 | 1.711 |

-continued

Dissolution of Compositions of the invention

| Example No. | Cimetidine (mg) | Glycerol Ester (Quantity-mg) | Lecithin | Sweetener | Dissolution (%)* 15' | 30' | 45' | 60' | Hardness (Newtons) | Weight (g) |
|---|---|---|---|---|---|---|---|---|---|---|
| 12+ | 200 | Monomuls (40) | — | Mannitol | 63 | 83 | 94 | 95 | 75.7 | 1.508 |
| 13** | 200 | Monomuls (40) | | Xylitol | 35 | 70 | 80 | 86 | 56.7 | 1.465 |

*US Pharmacopoeia-Paddle Test; 900 ml H$_2$O, 100 rpm, 37° C., tablets coarsely crushed in mortar before testing.
+ Examples 10 and 12 have essentially the same composition as Example 3 except that in Example 12, the glycerol ester is Monomuls rather than Dur EM.
**Examples 11 and 13 have essentially the same composition as Example 4 except that in Example 13, Monomuls has been substituted for Dur EM.

TABLE 1

Influence of various coating materials and coating processes on Cimetidine taste-masking and dissolution

| mg Cimetidine | Coating material | mg coating | Granulation in | Taste° masking | T$_{90}$% Cim.°° [Min.] |
|---|---|---|---|---|---|
| 100 | Precirol* | 50 | mixer | — | >>60 |
| 100 | Precirol | 100 | mixer | + | >>60 |
| 100 | Kollidon 25 | 5 | mixer | — | >60 |
| 100 | Dur EM | 10 | mixer | — | 20 |
| 100 | Dur EM | 15 | mixer | ± | 15 |
| 100 | Dur EM | 20 | mixer | + | 30–40 |
| 100 | Dur EM | 50 | mixer | + | 30–40 |
| 200 | Dur EM | 40 | mixer | + | 30–40 |
| 200 | Monomuls | 40 | mixer | + | 30–40 |
| 100 | Soyaphosphat. NC 95 H | 100 | mixer | + | >60 |
| 100 | Dur EM/ NC 95 H | 20 + 20 | mixer | + | 15–20 |
| 100 | Dur EM | 20 | spray dryer | — | <15 |
| 100 | Dur EM | 65 | spray dryer | — | 35–40 |
| 100 | Dur EM | 100 | spray dryer | + | 40–45 |
| 100 | Witepsol H 5 | 20 | mixer | — | |
| 100 | Witepsol W 45 | 20 | mixer | + | 30–35 |
| 100 | Glycerindist. | 20 | mixer | + | 40–45 |
| 100 | Crodesta F10 | 25 | mixer | + | >>60 |
| 100 | Crodesta F50 | 25 | mixer | + | 40–50 |
| 100 | Crodesta F160 | 25 | mixer | + | 40–50 |

*Precirol has a hydroxyl value in the range 90-110 and is composed of 40% (w/w) glyceryltripalmitostearate, 45% (w/w) glyceryldipalmitostearate, 14% (w/w) glycerylmonostearate and 1% (w/w) glycerol.
° + indicates no bitter taste ± indicates some residual bitterness but still palatable — indicates unpalatable bitterness
Results were obtained from a panel of four tasters who chewed tablets of a composition similar to those described in the Examples.
°°T$_{90}$% Cim. is the time taken for 90% of the cimetidine in the granules to dissolve under the conditions specified on pages 1243-1244 of the US Pharmacopoeia XXI.

EXAMPLES 14–15

Chewable Tablet Containing Cimetidine/Glycerol Ester Granules and Antacid

The following tablets were prepared according to the method described in Examples 1–7.

| | 14 | 15 |
|---|---|---|
| Cimetidine | 100.0 | 100.0 |
| Dur EM | 20.0 | 20.0 |
| Soyaphosphatide | — | 20.0 |
| F-MA 11* | 300.0 | 300.0 |
| Mg(OH)$_2$ | 200.0 | 200.0 |
| Mannitol | — | 642.5 |
| Sucrose | 670.3 | — |
| Microcrystalline Cellulose/ Sodium Carboxymethyl cellulose (Avicel RC 581) | 50.0 | 50.0 |
| Glycine | 25.0 | 25.0 |
| Sodium cyclamate | 50.0 | 50.0 |
| Sodium carboxymethyl cellulose (Blanose 7 HF) | 5.0 | 5.0 |
| Sodium chloride | 12.5 | 12.5 |
| Sodium glutamate | 5.0 | 5.0 |
| Hydroxypropylmethyl cellulose (Methocel E 5) | 25.0 | 25.0 |
| Calcium arachinate | 30.0 | 20.0 |
| Aerosil 200 | 3.0 | 3.0 |

-continued

| | 14 | 15 |
|---|---|---|
| Flavours | 4.2 | 25.0 |

*F-MA 11 is an aluminium hydroxide-magnesium carbonate co-dried gel.

We claim:

1. A pharmaceutical granule composition comprising from about 75 to 800 mg cimetidine and as a granulating agent and taste masking agent an ester of a polyhydroxy compound said polyhydroxy compound being a non-polymeric, non-aromatic hydrocarbon or carbohydrate having at least 2 hydroxyl groups per molecule, said composition providing a 90% by weight release of the cimetidine from the granule composition within about 50 minutes providing a 90% by weight release of the cimetidine from the granule composition within about 50 minutes.

2. A pharmaceutical granule composition according to claim 1 wherein the ester of a polyhydroxy compound is a glycerol ester or sucrose ester.

3. A pharmaceutical granule composition according to claim 2 which contains a glycerol ester in an amount corresponding to at least 15% by weight relative to the cimetidine; wherein the glycerol ester is selected from:

a) glycerol esters having a hydroxyl value of greater than 120;
b) glycerol esters having a hydroxyl value of greater than 60 and having less than 30% by weight triglyceride content; and
c) glycerol esters having a hydroxyl value of greater than 5 and a melting point of less than 40° C.

4. A composition according to claim 3 wherein the glycerol ester is present in an amount from 15% w/w to 100% w/w relative to the cimetidine.

5. A composition according to claim 4 wherein the amount of glycerol ester present is approximately 20% w/w relative to the cimetidine.

6. A composition according to claim 3 wherein the glycerol ester has a hydroxyl value of greater than 120.

7. A composition according to claim 4 wherein the glycerol ester has a hydroxyl value of greater than 120.

8. A composition according to claim 5 wherein the glycerol ester has a hydroxyl value of greater than 120.

9. A composition according to claim 6 wherein the glycerol ester is composed of more than 50% by weight of glyceryl monostearate.

10. A composition according to claim 1 containing a palatable pharmaceutically acceptable emulsifier.

11. A composition according to claim 10 wherein the emulsifier is a lecithin.

12. A composition according to claim 11 wherein the ester is a glycerol ester and the lecithin is present in an amount of up to approximately 200% w/w, for example approximately 100% w/w, relative to the glycerol ester.

13. A pharmaceutical granule composition according to claim 2 which contains a sucrose ester which is a mixture of mono-, di- and tri-esters with palmitic and stearic acids, the mixture having a hydroxyl value of greater than 130.

14. A chewable tablet containing a granule composition as defined in claim 1.

15. A chewable tablet containing a granule composition as defined in claim 3.

16. A pharmaceutical granule composition comprising a therapeutically effective non-toxic amount of cimetidine and an ester of a polyhydroxy compound, the ester being selected such that the bitter taste of cimetidine is substantially masked and such that 90% by weight of the cimetidine is releasable from the granule composition within about 50 minutes as measured using the US Pharmacopoeia paddle test (paddle speed 100 r.p.m.).

17. A pharmaceutical granule composition according to claim 16 which contains a glycerol ester in an amount corresponding to at least 15% by weight relative to the cimetidine; wherein the glycerol ester is selected from;
a) glycerol esters having a hydroxyl value of greater than 120;
b) glycerol esters having a hydroxyl value of greater than 60 and having less than 30% by weight triglyceride content; and
c) glycerol esters having a hydroxyl value of greater than 5 and a melting point of less than 40° C.

18. A composition according to claim 17 wherein the glycerol ester is present in an amount from 15% w/w to 100% w/w relative to the cimetidine.

19. A composition according to claim 18 which contains a lecithin.

20. A chewable tablet composition containing a granule composition as defined in claim 16.

* * * * *

UNITED STATES PATENT AND TRADEMARK OFFICE
CERTIFICATE OF CORRECTION

PATENT NO. : 5,057,319

DATED : October 15, 1991

INVENTOR(S) : Gottwald et al.

It is certified that error appears in the above-identified patent and that said Letters Patent is hereby corrected as shown below:

On column 3, line 29, "b" should be --5--.

On column 3, line 58, "and tri-esters. Particularly" should read --and tri-esters, particularly--.

On column 3, line 65, "Mumberside" should be --Humberside--.

On column 8, lines 59-61, claim 1, the following should be deleted from the claim "providing a 90% by weight release of the cimetidine from the granule composition within about 50 minutes".

Signed and Sealed this

Twenty-third Day of March, 1993

Attest:

STEPHEN G. KUNIN

Attesting Officer     Acting Commissioner of Patents and Trademarks